United States Patent
Gao

(10) Patent No.: US 10,518,950 B2
(45) Date of Patent: *Dec. 31, 2019

(54) ANTIMICROBIAL CABLE TIE

(71) Applicant: Thomas & Betts International LLC, Wilmington, DE (US)

(72) Inventor: Yan Gao, Memphis, TN (US)

(73) Assignee: Thomas & Betts International LLC, Wilmington, DE (US)

( * ) Notice: Subject to any disclaimer, the term of this patent is extended or adjusted under 35 U.S.C. 154(b) by 189 days.

This patent is subject to a terminal disclaimer.

(21) Appl. No.: 14/849,174

(22) Filed: Sep. 9, 2015

(65) Prior Publication Data

US 2016/0130054 A1 May 12, 2016

Related U.S. Application Data

(60) Provisional application No. 62/076,185, filed on Nov. 6, 2014.

(51) Int. Cl.
*B65D 63/10* (2006.01)
*B29C 35/02* (2006.01)
(Continued)

(52) U.S. Cl.
CPC .......... *B65D 63/1036* (2013.01); *B29C 35/02* (2013.01); *B65D 63/1027* (2013.01);
(Continued)

(58) Field of Classification Search
CPC ............ B65D 63/1036; B65D 63/1027; B65D 2563/101; A01N 25/10; A01N 25/34;
(Continued)

(56) References Cited

U.S. PATENT DOCUMENTS 5,102,075 A    4/1992  Dyer
5,513,421 A    5/1996  Wells
(Continued)

FOREIGN PATENT DOCUMENTS

EP    0919756 A2    6/1999
EP    1843070 A2    10/2007
(Continued)

OTHER PUBLICATIONS

Maureen Serafini "silver sodium hydrogen zirconium phosphate (Antimicrobial AlphaSan® RC 5000) NYS DEC Letter—Registration Jul. 2001" Jul. 5, 2001; http://pmep.cce.cornell.edu/profiles/miscpesticides/methylchloride-xanthangum/silver_sodium/silver_sodium_letter_701.html; printed Mar. 20, 2019; 2 pages (Year: 2019).*

(Continued)

*Primary Examiner* — Robert Sandy
*Assistant Examiner* — Louis A Mercado
(74) *Attorney, Agent, or Firm* — Taft Stettinius & Hollister LLP; J. Bruce Schelkopf

(57) ABSTRACT

Cable ties including an antimicrobial component and optionally a detectable component are disclosed. More particularly, cable ties including a composition having a base plastic, an antimicrobial additive and optionally a detectable additive selected from a detectable metal additive, an X-ray detectable additive and combinations thereof as well as methods of making the same are disclosed. Also, cable ties including an antimicrobial metallic barb and a composition having a base plastic and optionally an antimicrobial additive and/or a detectable additive selected from a detectable metal additive, an X-ray detectable additive and combinations thereof are disclosed.

8 Claims, 1 Drawing Sheet

(51) Int. Cl.
  *B29K 27/12* (2006.01)
  *B29K 27/06* (2006.01)
  *B29K 77/00* (2006.01)
  *B29K 71/00* (2006.01)
  *B29K 69/00* (2006.01)
  *B29K 505/10* (2006.01)
  *B29K 505/14* (2006.01)

(52) U.S. Cl.
  CPC ...... *B29K 2023/06* (2013.01); *B29K 2027/06* (2013.01); *B29K 2027/12* (2013.01); *B29K 2069/00* (2013.01); *B29K 2071/00* (2013.01); *B29K 2077/00* (2013.01); *B29K 2505/10* (2013.01); *B29K 2505/14* (2013.01); *B65D 2563/101* (2013.01)

(58) Field of Classification Search
  CPC ............... B29C 35/02; B29K 2505/14; B29K 2069/00; B29K 2071/00; B29K 2077/00; B29K 2027/06; B29K 2027/12; B29K 2023/06; B29K 2505/10
  See application file for complete search history.

(56) References Cited

U.S. PATENT DOCUMENTS

| | | | |
|---|---|---|---|
| 5,815,891 | A | 10/1998 | Students et al. |
| 7,017,237 | B2 | 3/2006 | Magno, Jr. et al. |
| 10,138,038 | B2 * | 11/2018 | Gao ................ B65D 63/1027 |
| 2004/0094243 | A1 * | 5/2004 | Wynne, III ............... C22C 9/04 |
| | | | 148/433 |
| 2006/0110456 | A1 | 5/2006 | Teo et al. |
| 2007/0226960 | A1 | 10/2007 | LaPorte et al. |
| 2007/0234525 | A1 | 10/2007 | LaPorte et al. |
| 2008/0044458 | A1 * | 2/2008 | MacDonald ........... A01N 59/16 |
| | | | 424/443 |
| 2008/0102122 | A1 * | 5/2008 | Mahadevan ........... A01N 59/16 |
| | | | 424/484 |
| 2009/0259251 | A1 | 10/2009 | Cohen |
| 2010/0239679 | A1 * | 9/2010 | Greene ................ A01N 25/26 |
| | | | 424/490 |
| 2012/0245629 | A1 * | 9/2012 | Gross ............... A61B 17/06166 |
| | | | 606/228 |
| 2015/0086597 | A1 * | 3/2015 | Mallak .................. A01N 59/20 |
| | | | 424/407 |
| 2015/0353250 | A1 | 12/2015 | Gao |

FOREIGN PATENT DOCUMENTS

| | | |
|---|---|---|
| EP | 2952094 A1 | 12/2015 |
| JP | 08090674 A | 4/1996 |
| JP | 10292107 A | 11/1998 |
| JP | 2003-073531 A | 3/2003 |
| JP | 2009-520076 A | 5/2009 |
| JP | 2011-513532 A | 4/2011 |
| JP | 2011-178416 A | 9/2011 |
| JP | 2014-088952 A | 5/2014 |
| WO | 2005061022 A2 | 7/2005 |
| WO | 2006015317 A1 | 2/2006 |
| WO | 2007/070650 A2 | 6/2007 |
| WO | 2008150460 A1 | 12/2008 |
| WO | 2009/108158 A1 | 9/2009 |
| WO | 2012027863 | 3/2012 |
| WO | 2013071474 A1 | 5/2013 |
| WO | 2013121169 A2 | 8/2013 |

OTHER PUBLICATIONS

Wikipedia, 'Antimicrobial copper-alloy touch surfaces', Internet Archive Oct. 19, 2010, https://web.archive.org/web/20101019203213/ https://en.wikipedia.org/wiki/Antimicrobial_copper-alloy_touch_surfaces.

* cited by examiner

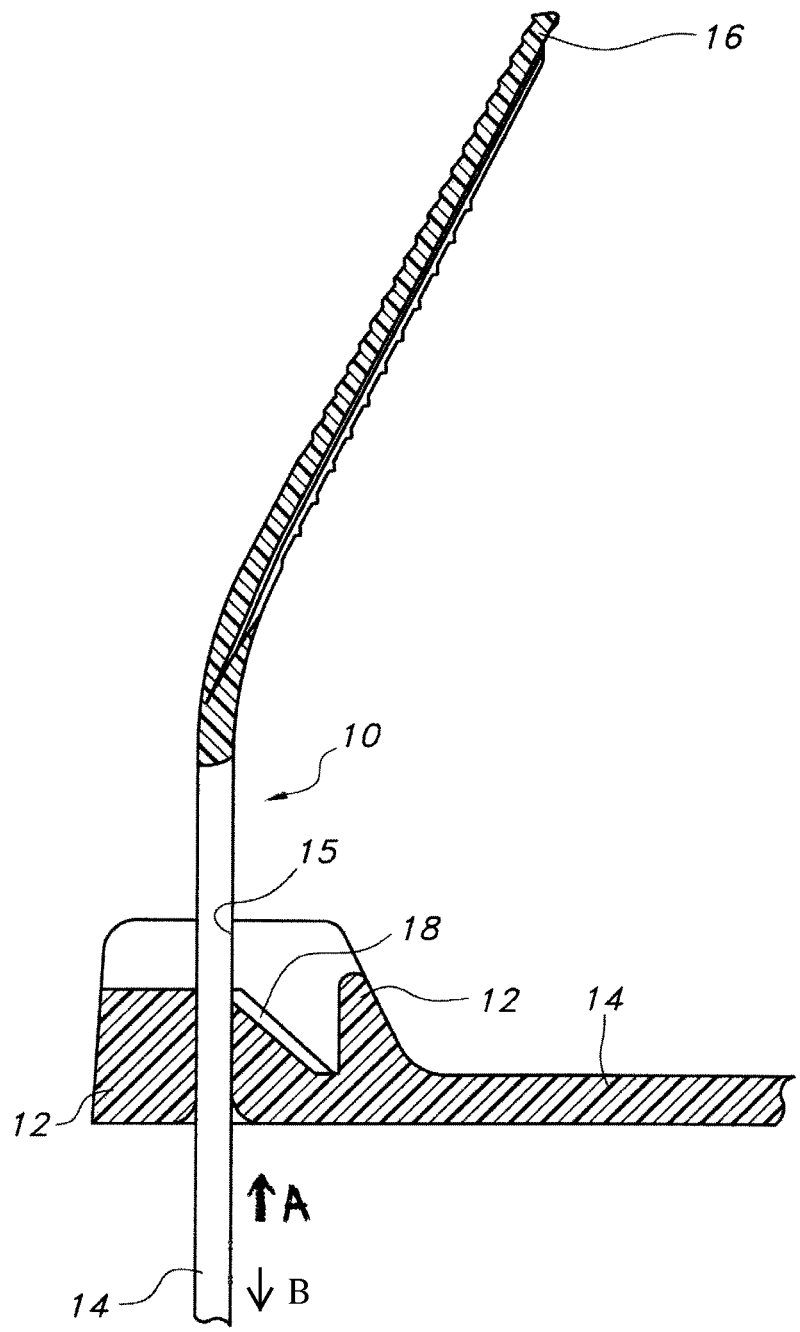

ANTIMICROBIAL CABLE TIE

FIELD OF THE INVENTION

The present invention relates to cable ties including an antimicrobial component and optionally a detectable component. More particularly, the present invention relates to cable ties including a composition having a base plastic (e.g., polyamide or polypropylene), an antimicrobial additive and optionally a detectable additive selected from a detectable metal additive, an X-ray detectable additive and combinations thereof as well as methods of making the same. The present invention also relates to cable ties including an antimicrobial metallic barb and a composition having a base plastic and optionally an antimicrobial additive and/or a detectable additive selected from a detectable metal additive, an X-ray detectable additive and combinations thereof.

BACKGROUND OF THE INVENTION

Cable ties are well known and may be used to bundle or secure a group of articles such as electrical wires or cables. Typically, cable ties include a head, elongate tail and a longitudinal strap therebetween. The head of the cable tie includes a locking element which is engageable with the strap to secure the strap in the head.

There are generally two types of cable ties. The first is a one-piece cable tie. The one-piece tie is integrally formed of plastic material, preferably polyamide, and uses a molded pawl inside the head and a formed teeth array in the strap body to secure the strap in the tail. The second is a two-piece cable tie. The two-piece tie has a polyamide head and strap body. A metallic (e.g., stainless steel) barb is embedded in the head which digs into the strap to secure the strap in the body.

Existing plastic cable ties allow the growth of bacteria and/or fungus on the surface thereof under normal atmospheric conditions. This is unfavorable in many applications where cable ties are widely used as fasteners. For example, in the typical high humidity and warm environment of a food processing facility, bacteria can grow on the surface of cable ties such that undesirable stains and odor develop over time. If introduced to a food ingredient during this process, such affected plastic cable tie could introduce bacterial and/or fungal contamination to the food ingredient before the affected cable tie is detected and separated from contact with any food or food ingredient. Likewise, a hospital environment, such as a surgery room, typically includes various medical equipment that use cable ties for harness purposes. Undesirably, different types of bacteria and/or fungi may be introduced to the surface of such cable ties by exposure, such as by direct contact and/or via air, from an infected individual and transmitted to other individuals (e.g., a patient or caregiver). Thus, there is a need for cable ties that exhibit antimicrobial properties.

SUMMARY OF THE INVENTION

The present invention provides cable ties including an antimicrobial component whereby the cable tie exhibits antimicrobial properties. In particular, the present invention provides cable ties including a composition having a base plastic and an antimicrobial additive.

The present invention further provides cable ties including an antimicrobial metallic barb and a composition including a base plastic.

The present invention also provides methods of preparing cable ties including the steps of: mixing ingredients including a base plastic and an antimicrobial additive to form a mixture; melting the mixture at a temperature that is between about 1 and about 30° C. above the melting point of the base plastic to form a molten material therefrom; and molding the cable tie from the molten material.

Advantageously, such cable ties provide protection from surface stain and odor caused by microbes (e.g., bacteria and/or fungi). Further, such cable ties reduce the possibility of microbial (e.g., bacterial and/or fungal) contamination, for example, in a food processing environment, when the cable tie is contacted with a food or food ingredient, or in a hospital environment, when the cable tie is exposed to a patient.

Additionally, in certain embodiments wherein the cable tie includes a detectable component that provides X-ray detectability and/or metal detectability, detection thereof is desirably enhanced.

BRIEF DESCRIPTION OF THE FIGURE

FIG. 1 shows, in section, an exemplary cable tie of the present invention, having a cable tie head and extending strap, with the strap inserted into the head.

DETAILED DESCRIPTION OF THE INVENTION

As used herein the following terms shall have the definitions set forth below.

As used herein, the term "antimicrobial component" refers to a component selected from an antimicrobial additive (as included in the composition of the cable tie), an antimicrobial metallic barb (as included in a two-piece cable tie) and the combination thereof.

As used herein, the term "detectable component" refers to a component selected from i) a detectable additive selected from a detectable metal additive, an X-ray detectable additive and combinations thereof (as included in the composition of the cable tie), ii) a metallic barb (as included in a two-piece cable tie) and iii) the combination thereof.

As used herein, the term "antimicrobial metallic barb" refers to a metallic barb suitable for use in a two-piece cable tie that includes an antimicrobial metallic barb material.

Referring to FIG. 1, a cable tie 10 of the present invention is shown. Cable tie 10 is typically an elongate molded plastic member which is used in a manner well known in the art to wrap around a bundle of articles (not shown).

In one embodiment, cable tie 10, includes a composition that includes a base plastic, an antimicrobial additive and optionally a detectable additive selected from a detectable metal additive, an X-ray detectable additive and combinations thereof, which in certain embodiments, is suitable for use with food and food grade materials. Cable tie 10 has a head 12 at one end thereof, a tail 16 at the other end of the head 12 and a generally planar strap 14 therebetween. In the illustrative embodiment provided, head 12 is formed as an integral portion of cable tie 10. However, in certain applications cable tie 10 may be constructed in a manner where head 12 is formed separately from strap 14.

Head 12 of cable tie 10 includes an aperture 15 therethrough (shown with strap 14 therein) for insertably accommodating the tail 16 and passage of the strap 14 therein in a first direction "A". Head 12 of cable tie 10 includes a locking device 18 supported by the head 12 and extending into the aperture. The locking device permits movement of the strap 14 in the first direction "A" and prevents substantial movement of the strap 14 in a second direction "B" opposite the first direction upon an attempt to withdraw the strap 14 from the aperture. The locking device may include a metallic barb such as shown in U.S. Pat. No. 5,513,421; or an integrally formed plastic pawl such as shown in U.S. Pat. No. 7,017,237.

In another embodiment, cable tie 10 includes an antimicrobial metallic barb and a composition that includes a base plastic and optionally an antimicrobial additive and/or a detectable additive selected from a detectable metal additive, an X-ray detectable additive and combinations thereof, which in certain embodiments, is suitable for use with food and food grade materials.

Suitable base plastics include, but are not limited to, polyamide (e.g., nylon), polypropylene, polycarbonate, poly (ethylene tetrafluoroethylene), polyetheretherketone, poly (ethylene and chlorotrifluoroethylene), polyvinyl chloride and combinations of two or more thereof. Base plastic is loaded at between about 90 to about 110 phr. In one embodiment, the base plastic is polypropylene. In one embodiment, the base plastic is polyamide. In one embodiment, the base plastic is polyamide 6 (i.e., nylon 6). In one embodiment, the base plastic is polyamide 6,6 (i.e., nylon 6,6). In one embodiment, base plastic is polyamide 6,6 loaded at between about 90-100 phr. In one embodiment, polyamide 6,6 is loaded at about 100 phr. In one embodiment, polyamide 6,6 loaded at about 100 phr is a medium impact modified compound with embedded process aid. In one embodiment, polyamide 6,6 loaded at about 100 phr is an unfilled resin with embedded process aid.

Suitable antimicrobial additives include, but are not limited to, silver ion complex, copper ion complex, polychloro phenoxy phenol derivative, quaternary ammonium compound, zinc pyrithione derivative and combinations of two or more thereof. In one embodiment, the antimicrobial additive is loaded at between about 0.01 phr and about 15 phr, preferably between about 0.05 phr and about 10 phr, more preferably between about 0.1 phr and about 7.5 phr and most preferably between about 0.2 phr and about 5 phr. In some embodiments, the antimicrobial additive is loaded at about 1 phr or about 2 phr or between about 1 phr and about 2 phr. In one embodiment, the antimicrobial additive is silver sodium hydrogen zirconium phosphate. In one embodiment, the antimicrobial additive is silver sodium hydrogen zirconium phosphate loaded at between about 0.2 phr and about 5 phr. In one embodiment, the antimicrobial additive is silver sodium hydrogen zirconium phosphate loaded at 1 about phr. As is well known to a skilled artisan, the amount of antimicrobial additive in the composition can be varied, depending on the antimicrobial additive selected and/or other ingredients employed, so as to provide antibacterial properties against bacteria and/or fungus to the resultant cable tie.

Suitable detectable metal additives include, but are not limited to, ferrous metal particles, non-ferrous metal particles and combinations of two or more thereof. In one embodiment, the detectable metal additive is iron particles. Iron particles, other ferrous metal particles and/or non-ferrous particles can have various shapes (e.g., spherical shape, flake shape or other irregular shapes). The particle size of detectable metal additives can range from between about 25 µm and about 1,000 µm, preferably between about 50 µm and about 750 µm, more preferably between about 100 µm and about 500 µm, even more preferably between about 150 µm and about 200 µm. Detectable metal additives are loaded at between about 0.1 phr and about 50 phr, preferably between about 0.25 phr and about 40 phr, more preferably between about 0.5 phr and about 35 phr, even more preferably between about 0.75 phr and about 30 phr, yet even more preferably between about 1 phr and about 25 phr and most preferably between about 15 phr and about 25 phr. In a preferred embodiment, the metal additive is loaded at about 21 phr. In one embodiment, the detectable metal additive is iron particles having a particle size range of from about 150 µm to about 200 µm. In other embodiments, the detectable metal additive is iron particles having a particle size range of from about 150 µm to about 200 µm loaded at about 21 phr. As is well known to a skilled artisan, the amount of detectable metal additive in the composition can be varied, depending on shape and size of particles thereof, to provide metal detectability to the resultant cable tie.

Suitable X-ray detectable additives include, but are not limited to, one or more iodine based salts, one or more barium based salts and combinations of two or more thereof. In one embodiment, the X-ray detectable additive is barium sulfate. In one embodiment, X-ray detectable additive is loaded at between about 4 phr to about 8 phr. In one embodiment, the X-ray detectable additive is barium sulfate powder loaded at between about 4 phr to about 8 phr. In one embodiment, barium sulfate is loaded at about 7 phr. As is well known to a skilled artisan, the amount of X-ray detectable additive in the composition can be varied, depending on other ingredients, to provide X-ray detectability to the resultant cable tie.

Suitable antimicrobial metallic barb materials include, but are not limited to, copper alloy with an amount of copper between about 62% and about 99.99% therein (e.g., C11000, C51000, C70600, C26000, C75200, and C28000). In one embodiment, the antimicrobial metallic barb material includes C28000 copper. As is well known to a skilled artisan, the amount of antimicrobial metallic barb material can be varied, depending on the antimicrobial metallic barb material selected and/or other ingredients employed in the cable tie, so as to provide antibacterial properties against bacteria and/or fungus to the resultant cable tie.

In one embodiment, the cable tie includes a composition having a base plastic, an antimicrobial additive and optionally a detectable additive selected from a detectable metal additive, an X-ray detectable additive and combinations thereof. In one embodiment, the composition of the cable tie includes a detectable additive selected from a detectable metal additive, an X-ray detectable additive and combinations thereof. In one such embodiment, the detectable metal additive is iron particles and the X-ray detectable additive is barium sulfate. In one embodiment, the cable tie is a one-piece cable tie (i.e., without a metallic barb). In one embodiment, the cable tie further includes a metallic barb and is thereby a two-piece cable tie. In one such embodiment, the metallic barb is an antimicrobial metallic barb.

In one embodiment, the cable tie is a two-piece cable tie and includes an antimicrobial metallic barb and a composition having a base plastic and optionally an antimicrobial additive and/or a detectable additive selected from a detectable metal additive, an X-ray detectable additive and combinations thereof. In one embodiment, the cable tie is a two piece cable tie and includes an antimicrobial metallic barb and a composition having a base plastic. In one embodiment, the composition of the cable tie further includes an antimicrobial additive. In one embodiment, the composition of the cable tie further includes a detectable additive selected from a detectable metal additive, an X-ray detectable additive and combinations thereof. In one such embodiment, the detectable metal additive is iron particles and the X-ray detectable additive is barium sulfate. In one embodiment, the composition of the cable tie further includes both an antimicrobial additive and a detectable additive selected from a detectable metal additive, an X-ray detectable additive and combinations thereof.

In one embodiment, the cable tie includes a composition having a base plastic and an antimicrobial additive. In one embodiment, the base plastic is polyamide, polypropylene, polycarbonate, poly(ethylene tetrafluoroethylene), polyetheretherketone, poly(ethylene and chlorotrifluoroethylene), polyvinyl chloride, or a combination of two or more thereof. In one embodiment, the antimicrobial additive is selected from the group consisting of silver ion complex, copper ion complex, polychloro phenoxy phenol derivative, quaternary ammonium compound, zinc pyrithione derivative and combinations of two or more thereof. In one embodiment, the antimicrobial additive is loaded at between about 0.01 phr to about 15 phr, preferably between about 0.05 phr and about 10 phr, more preferably between about 0.1 phr and about 7.5 phr and most preferably between about 0.2 phr and about 5 phr. In some embodiments, the antimicrobial additive is loaded at about 1 phr or about 2 phr or between about 1 phr and about 2 phr. In one embodiment, the antimicrobial additive is silver sodium hydrogen zirconium phosphate. In one embodiment, the composition of the cable tie further includes a detectable additive selected from a detectable metal additive, an X-ray detectable additive and combinations thereof. In one embodiment, the composition of the cable tie includes a detectable additive, wherein the detectable additive includes a combination of a detectable metal additive and an X-ray detectable additive. In one such embodiment, the detectable metal additive is iron particles and the X-ray detectable additive is barium sulfate. In one embodiment, the cable tie is a one-piece cable tie (i.e., without a metallic barb). In one embodiment, the cable tie further includes a metallic barb and is thereby a two-piece cable tie. In one such embodiment, the metallic barb is an antimicrobial metallic barb. In one embodiment, the antimicrobial metallic barb includes the antimicrobial metallic barb material C28000.

In one embodiment, the base plastic is polyamide 6,6, and the antimicrobial additive is silver sodium hydrogen zirconium phosphate. In one such embodiment, the base plastic is polyamide 6,6 loaded at about 100 phr, and the silver sodium hydrogen zirconium phosphate is loaded at about 1 phr. In one embodiment, the composition of the cable tie further includes a detectable additive selected from a detectable metal additive, an X-ray detectable additive and combinations thereof. In one embodiment, the detectable metal additive is iron particles and the X-ray detectable additive is barium sulfate. In one such embodiment, the base plastic is polyamide 6,6 loaded at about 100 phr, the silver sodium hydrogen zirconium phosphate is loaded at about 1 phr, the iron particles have a size range of about 150 pm to about 200 pm and are loaded at about 21 phr, and the barium sulfate is loaded at about 7 phr. In one embodiment, the cable tie is a one-piece cable tie. In one embodiment, the cable tie further includes a metallic barb and is thereby a two-piece cable tie. In one such embodiment, the metallic barb is an antimicrobial metallic barb. In one embodiment, the antimicrobial metallic barb includes the antimicrobial metallic barb material C28000.

In one embodiment, the cable tie includes an antimicrobial metallic barb and a composition having a base plastic. In one embodiment, the base plastic is polyamide, polypropylene, polycarbonate, poly(ethylene tetrafluoroethylene), polyetheretherketone, poly(ethylene and chlorotrifluoroethylene), polyvinyl chloride, or a combination of two or more thereof. In one embodiment, the base plastic is polyamide 6,6. In one embodiment, the composition of the cable tie further includes a detectable additive selected from a detectable metal additive, an X-ray detectable additive and combinations thereof. In one embodiment, the detectable metal additive is iron particles, and the X-ray detectable additive is barium sulfate.

In one embodiment, the composition of the cable tie further includes a colorant. A skilled artisan can readily select a colorant compatible with the composition. In one embodiment, the colorant is loaded at between about 0.1 phr and about 50 phr, preferably between about 0.25 phr and about 40 phr, more preferably between about 0.5 phr and about 30 phr, even more preferably between about 0.75 phr and about 20 phr, yet even more preferably between about 1 phr and about 10 phr, and most preferably between about 1 phr and about 8 phr.

In one embodiment, any of the aforementioned cable ties of the present invention are treated with sanitizing chemical to inhibit antimicrobial (e.g., bacterial and/or fungal) growth. For example, sanitizing chemical can be applied once, daily, every other day or as deemed necessary to inhibit antimicrobial growth. In one embodiment, a cable tie of the present application is sanitized with about 0.1% sodium hypochlorite (NaClO) aqueous solution (widely used in hospital environments as a cleaning agent), for example, every other day. As is well known to a skilled artisan, sterilization procedures compatible for cleaning plastic cable ties may be employed so as to minimize bacterial and/or fungal growth.

In general, methods of preparing cable ties are provided which include (a) mixing ingredients including a base plastic, an antimicrobial additive and optionally a detectable additive selected from a detectable metal additive, an X-ray detectable additive and combinations thereof to form a mixture; (b) melting the mixture at a temperature that is between about 1 and about 30° C. above the melting point of the base plastic to form a molten material therefrom and (c) molding the cable tie from the molten material. Technology that forms such composition is well known to a skilled artisan. Likewise, molding process technology for cable tie products is well known to a skilled artisan.

More specifically, the present invention provides methods of preparing a cable tie including mixing the ingredients (including a base plastic, an antimicrobial additive, and optionally a detectable additive selected from a detectable metal additive, an X-ray detectable additive and combinations thereof) mechanically, followed by a heated melting process that undergoes further pressurized mechanical mixing to form a molten mixture wherein the temperature is controlled at between about 1 and about 30° C. above the melting point of the base plastic. The molten material is pressed flowing into a twin screw extrusion machine thereby forming a continuous rod which is subsequently cut into smaller pellets as raw compound material. The compound material is then re-melted in a regular injection machine with a single screw, and subsequently pressed flowing into a steel mold thereby forming a cable tie shape. The molded material is cooled down to yield a cable tie exhibiting antimicrobial properties.

Though not meant to be limited by any theory with the subject invention, it is believed that incorporation of an antimicrobial additive in a composition from which a cable tie is molded and/or inclusion of an antimicrobial metallic barb provides antimicrobial properties thereto. In particular, it is believed that such cable ties exhibit reduced surface stain and odor caused by bacteria and/or fungus. Further, it is believed that such cable ties reduce the possibility of microbial (e.g., bacterial and/or fungal) contamination when the cable ties are contacted with or exposed to a food, a food ingredient, or an individual.

As is well known to a skilled artisan, metal detectability of a cable tie can be tested using a metal detector. In one embodiment, a metal detecting device is able to detect a cable tie of the present invention at a setting of 0.170 cm/ferrous sphere.

As is well known to a skilled artisan, X-ray detectability of a cable tie can be tested using an X-ray detector. In one embodiment, an X-ray detecting device (e.g., Eagle FA detector from Smith-Heimann) is able to detect the presence of a cable tie of the present invention.

As is well known to a skilled artisan, antimicrobial properties of a cable tie of the present invention can be ascertained by measuring growth of a representative microbe thereon following incubation under conditions conducive to microbial growth as compared with a similarly treated conventional cable tie (i.e., lacking an antimicrobial additive). In one embodiment, a cable tie of the present invention is subjected to an antimicrobial test following either JIS Z2801 or iso22196 testing standard for representative bacteria. Desirably, a cable tie of the present invention will exhibit a >99.9% reduction of *Escherichia coli* and >99% reduction of *Staphylococcus aureus*. In another embodiment, a cable tie of the present invention exhibits the aforementioned antimicrobial activity and further exhibits favorable aging under accelerated aging conditions. For example, accelerated aging conditions for a polyamide 6,6-based antimicrobial cable tie are 60° C. and 50% relative humidity for 54 days, equating to two years of regular application at normal atmosphere. Additionally, antimicrobial activity and accelerated aging conditions may include treatment with about 0.1% sodium hypochlorite (NaClO) aqueous solution every other day as this treatment is widely used in a hospital environment as a cleaning agent.

Numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

All documents, patents and other literature referred to herein are incorporated by reference in their entirety.

The term "comprising" as may be used in the following claims is an open-ended transitional term that is intended to include additional elements not specifically recited in the claims. The term "consisting essentially of" as may be used in the following claims is a partially closed transitional phrase and is intended to include the recited elements plus any unspecified elements that do not materially affect the basic and novel characteristics of the claims. For example, the cable tie may be embossed or printed with indicia and still be included in the meaning of "consisting essentially of", even if not specifically recited. The term "consisting of" as may be used in the following claims is intended to indicate that the claims are restricted to the recited elements.

It should be noted that it is envisioned that any feature, element or limitation that is positively identified in this document may also be specifically excluded as a feature, element or limitation of an embodiment of the present invention.

It will be appreciated by those skilled in the art that changes could be made to the embodiments described above without departing from the broad inventive concept thereof. It is understood, therefore, that this invention is not limited to the particular embodiments disclosed, but is intended to cover modifications that are within the spirit and scope of the invention, as defined by the appended claims.

What is claimed is:

1. A two-piece cable tie comprising:
   i) a composition wherein the composition consists essentially of:
      a) a base plastic, wherein the base plastic is polyamide,
      b) an antimicrobial additive mixed with the base plastic, and wherein the antimicrobial additive is silver sodium hydrogen zirconium phosphate, and
      c) a detectable additive selected from a detectable metal additive, an X-ray detectable additive and combinations thereof, and
   ii) a metallic barb,
   wherein the metallic barb is an antimicrobial metallic barb comprising a copper alloy selected from the group consisting of C28000, C11000, C51000, C70600, C26000, and C75200.

2. The cable tie of claim 1, wherein the antimicrobial additive is loaded at between 0.2 phr and about 5 phr.

3. A method of preparing the cable tie of claim 1, the method comprising the steps of:
   mixing ingredients comprising the base plastic and the antimicrobial additive to form a mixture;
   melting the mixture at a temperature that is between about 1 and about 30° C. above a melting point of the base plastic to form a molten material therefrom; and
   molding the cable tie from the molten material.

4. The method of claim 3, wherein the base plastic is polypropylene, polycarbonate, poly(ethylene tetrafluoroethylene), polyetheretherketone, poly(ethylene and chlorotrifluoroethylene), polyvinyl chloride, or a combination of two or more thereof.

5. The method of claim 3, wherein the antimicrobial additive is loaded at between about 0.2 phr and about 5 phr.

6. The cable tie of claim 1, wherein the silver sodium hydrogen zirconium phosphate is loaded at 1 phr.

7. The cable tie of claim 6, wherein the polyamide is loaded at 100 phr.

8. The cable tie of claim 7, wherein the detectable additive is the combination of iron particles having a size range of 150 pm to 200 pm loaded at 21 phr and barium sulfate loaded at 7 phr.

* * * * *